United States Patent [19]

Kaiser et al.

[11] 4,354,029

[45] Oct. 12, 1982

[54] PREPARATION OF 2-SUBSTITUTED-2-OXAZOLINES WITH ORGANIC ZINC SALT CATALYSTS

[75] Inventors: Mark E. Kaiser, Midland, Mich.; David L. Larson, Cookeville, Tenn.

[73] Assignee: The Dow Chemical Company, Midland, Mich.

[21] Appl. No.: 325,948

[22] Filed: Nov. 30, 1981

Related U.S. Application Data

[63] Continuation of Ser. No. 966,696, Dec. 5, 1978, abandoned, which is a continuation-in-part of Ser. No. 758,279, Jan. 10, 1977, abandoned, and Ser. No. 875,280, Feb. 6, 1978, abandoned.

[51] Int. Cl.³ .......................................... C07D 263/12
[52] U.S. Cl. ................................................ 548/239
[58] Field of Search ........................................ 548/239

[56] References Cited

U.S. PATENT DOCUMENTS

| 3,813,378 | 5/1974 | Whitte et al. | 548/239 |
| 3,917,631 | 11/1975 | Arlt | 548/239 |
| 4,014,880 | 3/1977 | Dowd et al. | 548/239 |
| 4,035,309 | 7/1977 | Brois | 548/239 |

FOREIGN PATENT DOCUMENTS

1483682  8/1977  United Kingdom.

Primary Examiner—Anton H. Sutto
Attorney, Agent, or Firm—Charles J. Enright

[57] ABSTRACT

2-Substituted-2-oxazolines are prepared by contacting N-(2-hydroxyalkyl)carboxamides with a small but catalytic amount of an organic zinc salt at an elevated temperature.

8 Claims, No Drawings

PREPARATION OF 2-SUBSTITUTED-2-OXAZOLINES WITH ORGANIC ZINC SALT CATALYSTS

CROSS-REFERENCE TO RELATED APPLICATIONS

This application is a continuation of abandoned application Ser. No. 966,696, filed Dec. 5, 1978, which is a continuation-in-part of abandoned application Ser. No. 758,279, filed Jan. 10, 1977, and copending application Ser. No. 875,280, filed Feb. 6, 1978, now abandoned.

BACKGROUND OF THE INVENTION

2-Substituted-2-oxazolines form a known class of compounds having many members and many utilities. The chemistry of such oxazolines has been summarized, for example, by Wiley et al., Chemical Reviews, Vol. 44, 447 (1949), by Seeliger et al., Angew. Chem. International Edition, Vol. 5, No. 10, 875 (1966), and by Frump, Chemical Reviews, Vol. 71, No. 5, 483 (1971). Patents on monomeric oxazolines have been classified by the U.S. Patent and Trademark Office under 260/307F.

One of the prior art processes for preparing 2-substituted-2-oxazolines is the cyclodehydration of N-($\beta$-hydroxyalkyl)carboxamides. This cyclodehydration occurs in vapor phase over alumina (U.S. Pat. No. 3,562,263 and Frump vide supra, page 485) and in liquid phase over certain salts of manganese, cobalt, rare earth metals, molybdenum and tungsten (U.S. Pat. Nos. 3,681,329 and 3,681,333). The latter two patents indicate that the cyclodehydration reaction is brought about by heating the hydroxyamide and catalyst together in a distillation apparatus from which the oxazoline product distills from the reaction mixture as it is formed along with the by-product water.

In another process, Ghera et al., J. Chem. Soc., Chem. Commun., No. 11, 639 (1972) teach that 2-substituted-2-oxazolines are prepared by heating N-(2-hydroxyalkyl)-carboxamides in the presence of solid zinc acetate. Experimentally, the authors heated the carboxamide reactant with a ten-fold excess of powdered anhydrous zinc acetate in a glass tube under a constant flow of nitrogen and atmospheric pressure. This resulted in a formation of a 1:1 complex of oxazoline with zinc acetate which was isolated. The complexes were subsequently decomposed in a separate step into oxazolines by treatment with water or filtration through a Florisil column.

SUMMARY OF THE INVENTION

A new process for making 2-substituted-2-oxazolines has now been discovered. The new process comprises reacting by contacting in a liquid phase an N-(2-hydroxyalkyl)carboxamide with a small but catalytic amount of an organic zinc salt. The temperature/pressure relationship is normally adjusted such that the oxazoline and water codistill from the reaction mixture essentially as fast as they are formed.

DETAILED DESCRIPTION OF THE INVENTION

The N-($\beta$-hydroxyalkyl)carboxamides used in the instant process are a known class of compounds which can be represented by the formula

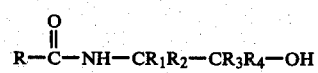

wherein R is a hydrocarbon or an inertly-substituted hydrocarbon group and $R_1$–$R_4$ are hydrogen or inert organic radicals. By "inert" is meant inert in the instant process. Such carboxamides are typically prepared by reacting a carboxylic acid (RC(O)OH) or a lower alkyl ester of the carboxylic acid with an ethanolamine of the formula $$NH_2-CR_1R_2-CR_3R_4-OH \quad (II)$$

wherein $R_1$–$R_4$ have the aforesaid meaning. The carboxylic acid/amine salt which is formed initially in these reactions can be used in the instant process in place of the carboxamide. When such carboxylic acid/amine salts are used, the carboxamide is generated in situ. In formulas I and II, $R_3$ and $R_4$ are each preferably hydrogen and $R_1$ and $R_2$ are hydrogen, lower alkyl ($C_1$–$C_6$), hydroxymethyl or alkanoyloxymethyl (alkyl—C(O)—O—$CH_2$—) groups of up to about 17 carbon atoms. More preferably, $R_1$–$R_4$ are each hydrogen. These preferences are based upon the commercial availability of the ethanolamines. R in formula I is preferably alkyl of from 1 to about 17 carbon atoms or phenyl and is more preferably methyl, ethyl or phenyl and is most preferably methyl or ethyl. Examples of suitable N-($\beta$-hydroxyalkyl)carboxamides include compounds of formula I having the following values for R and $R_1$–$R_4$:

TABLE I

| R | $R_1$ | $R_2$ | $R_3$ | $R_4$ |
|---|---|---|---|---|
| $CH_3$ | H | H | H | H |
| $CH_3$ | $C_4H_9$ | H | H | H |
| $CH_3$ | $C_2H_5$ | $C_2H_5$ | H | H |
| $C_2H_5$ | H | H | H | H |
| $C_2H_5$ | $CH_2OH$ | $CH_2OH$ | H | H |
| $C_2H_5$ | $CH_2O(O)C-C_{17}H_{35}$ | H | H | H |
| $C_3H_7$ | $C_6H_5$ | H | $C_6H_5$ | H |
| $C_7H_{15}$ | $CH_3$ | H | H | H |
| $C_9H_{19}$ | $CH_3$ | $CH_3$ | H | H |
| $C_{11}H_{23}$ | $CH_3$ | H | $CH_3$ | H |
| $C_{17}H_{35}$ | H | H | H | H |
| $C_6H_5$ | H | H | H | H |
| $C_6H_4CH_3$ | $C_6H_5$ | H | $CH_3$ | H |
| $C_6H_5CH_2$ | H | H | $CH_3$ | $CH_3$ |
| $CH_3(CH_2)_7CH=CH(CH_2)_7$ | H | H | H | H |
| cyclohexyl | H | H | H | H | and other like compounds.

The catalysts in the instant cyclodehydration reaction are organic zinc salts which are soluble in the carboxamide reactant or liquid reaction medium. The term "soluble" is not meant to imply that the zinc salt is soluble or miscible in all proportions with the carboxamide or liquid reaction medium but instead has at least a minimum solubility (e.g., about 100 parts per million or more) at reaction temperature. Such zinc salts are used in the process in small but catalytic amounts. Normally, the zinc salts are charged in amounts of from about 0.005 to about 0.4 mole of zinc salt per mole of carboxamide reactant but more or less of the zinc salts can be used, if desired. Carboxylic acid salts of zinc having the formula $(RCOO^-)_2Zn^{++}$ wherein R is a $C_1$–$C_{20}$ aliphatic or alicyclic radical or an inertly-substituted $C_1$–$C_{20}$ aliphatic or alicyclic carboxylic acid radical may be used as catalysts in the invention. Suitable carboxylic acid zinc salts include, for example, zinc acetate, zinc formate, zinc propionate, zinc stearate, zinc neodecanoate, and the like. Zinc acetate is the current preferred catalyst.

The instant cyclodehydration reaction may be conducted neat or in solution with a suitable inert solvent. By "inert" is meant inert in the process. Suitable such inert solvents include, for example, chlorinated hydrocarbon solvents, aromatic hydrocarbons, cycloaliphatic hydrocarbons, aliphatic hydrocarbons, and the like. We prefer, however, to conduct the reaction neat (i.e., that is without any solvent added).

The reaction temperature must, obviously, be sufficient to promote the cyclodehydration reaction and is normally selected in the range of from about 140° C. to about 280° C. Preferred reaction rates have been observed at temperatures of from about 160° C. to about 250° C. The instant cyclodehydration reaction is also preferably conducted under reduced pressure. This facilitates product recovery in that frequently a reaction temperature may be chosen which is above the boiling point of the 2-substituted-2-oxazoline product and below the boiling point of the N-($\beta$-hydroxyalkyl)carboxamide. In this manner, the 2-substituted-2-oxazoline can be removed from the reaction mixture as a volatile gas essentially as fast as it is formed. This is very desirable since the instant cyclodehydration reaction is a reversible process and by removing the products, the reaction is forced to completion by substantially reducing the reverse reaction. Water normally codistills with the 2-substituted-2-oxazoline product.

The instant process may be conducted in a batch process or by a continuous process. In the preferred continuous process, of course, the N-($\beta$-hydroxyalkyl)carboxamide reactant is metered into the reaction vessel at essentially the same rate as the 2-substituted-2-oxazoline and water are removed.

EXPERIMENTAL

The following examples will further illustrate the invention.

EXAMPLE 1

Preparation of 2-Ethyl-2-Oxazoline Over Zinc Acetate Dihydrate

Zinc acetate dihydrate (10.0 g; 0.045 mole) and 95.4 percent pure N-($\beta$-hydroxyethyl)propionamide (20.0 g; 0.162 mole) were charged to a reaction vessel equipped with a stirring means, a metering pump, and a 5-plate Oldershaw distillation column with a take-off head. The pressure over the reaction mixture was adjusted to 50 mm Hg and the reaction mixture heated to 200° C. The reaction mixture was held at 200° C. and 95.4 percent pure N-($\beta$-hydroxyethyl)propionamide (290 g; 2.35 mole) was pumped in at approximately 0.9 g/min to the system. As the propionamide was added to the reaction mixture, a water-white distillate was collected overhead through the distillation apparatus at a head temperature of 40° C.–45° C. After the addition of the propionamide was complete, the pot was heated to 220° C. to drive off the last amounts of 2-ethyl-2-oxazoline. The overhead distillate temperature reached a maximum of 41° C. during this post-heating step. A total of 294.8 g of water-white distillate was thus obtained overhead leaving 21.7 g of a tan, wet paste remaining in the pot. Analysis of the distillate overheads by gas chromatography using an internal standard and also a Karl Fischer water titration showed the material to be 2-ethyl-2-oxazoline, water and very minor amounts of unreacted propionamide and 2-methyl-2-oxazoline. The impurities in the propionamide reactant were: water (approximately 1 percent); monoethanolamine (approximately 2–3 percent); and the amidoester of propionic acid and monoethanolamine (approximately 1 percent).

The oxazoline was produced in 96.2 percent yield, based on the pure N-($\beta$-hydroxyethyl)propionamide charged to the system. The amount of water produced according to analysis was 93.0 percent of theory. The 2-ethyl-2-oxazoline can be easily separated from the mixture by selective extraction using diethylbenzene followed by distillation.

EXAMPLE 2

In another experiment, 2-ethyl-2-oxazoline was prepared in 82 percent yield by warming a propionic acid/ethanolamine salt in the presence of approximately 2 mole percent zinc acetate dihydrate at a temperature of 200° C./50 mm Hg. This was a batch experiment in which the acid/amine salt and catalyst were initially charged and warmed to the indicated reaction temperature. There was a pause in the rise in temperature during which the acid/amine salt was converted to the amide. Otherwise, this reaction proceeded essentially the same as Example 1 above. The product was similarly recovered as an overhead distillate with water.

Other catalysts and carboxamide reactants as set forth above could be similarly used to produce the 2-substituted-2-oxazolines.

What is claimed is:

1. A cyclodehydration process for making a 2-substituted-2-oxazoline comprising reacting by contacting in liquid phase a N-(2-hydroxyalkyl)carboxamide corresponding to the formula

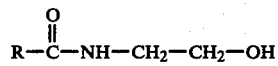

wherein R is alkyl of 1 to about 17 carbon atoms or phenyl, or a carboxylic acid/amine salt precursor of said N-(2-hydroxyalkyl)carboxamide with a small but catalytic amount of an organic zinc salt.

2. The process defined by claim 1 wherein R is methyl, ethyl or phenyl.

3. The process defined by claim 2 wherein R is methyl or ethyl.

4. The process defined by claim 1 wherein said catalyst is charged in amounts of from about 0.005 to about 0.4 mole or organic zinc salt per mole of carboxamide reactant.

5. The process defined by claim 1 wherein said catalyst is zinc acetate or zinc neodecanoate.

6. The process defined by claim 1 wherein the process is conducted under conditions of temperature and pressure such that the 2-substituted-2-oxazoline product is removed from the reaction mixture as a volatile gas essentially as it is formed.

7. The process defined by claim 6 wherein said catalyst is zinc acetate and wherein said carboxamide is N-(2-hydroxyethyl)propionamide.

8. The process defined by claim 7 wherein said zinc acetate is charged in amounts of from about 0.005 to about 0.4 mole of organic zinc salt per mole of carboxamide reactant.

* * * * *